United States Patent
Clark et al.

(10) Patent No.: US 9,981,948 B2
(45) Date of Patent: May 29, 2018

(54) CRYSTALLINE SALTS OF (S)-6-((1-ACETYLPIPERIDIN-4-YL)AMINO)-N-(3-(3,4-DIHYDROISOQUINOLIN-2(1H)-YL)-2-HYDROXYPROPYL)PYRIMIDINE-4-CARBOXAMIDE

(71) Applicant: GLAXOSMITHKLINE INTELLECTUAL PROPERTY DEVELOPMENT LIMITED, Brentford, Middlesex (GB)

(72) Inventors: William M. Clark, King of Prussia, PA (US); Rajendra S. Sathe, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days. days.

(21) Appl. No.: 15/840,086

(22) Filed: Dec. 13, 2017

(65) Prior Publication Data

US 2018/0099948 A1 Apr. 12, 2018

Related U.S. Application Data

(63) Continuation of application No. 15/318,714, filed as application No. PCT/IB2015/054712 on Jun. 23, 2015, now Pat. No. 9,884,846.

(60) Provisional application No. 62/016,819, filed on Jun. 25, 2014.

(51) Int. Cl.
*C07D 401/14* (2006.01)
*A61K 9/00* (2006.01)
*A61K 31/506* (2006.01)

(52) U.S. Cl.
CPC .......... *C07D 401/14* (2013.01); *A61K 9/0053* (2013.01); *A61K 31/506* (2013.01); *C07B 2200/13* (2013.01)

(58) Field of Classification Search
CPC ............................ C07D 401/14; A61K 31/506
USPC .................................. 544/328, 329; 514/256
See application file for complete search history.

(56) References Cited

U.S. PATENT DOCUMENTS 8,993,555 B2   3/2015   Duncan

FOREIGN PATENT DOCUMENTS

WO    WO 2011/079236 A1    6/2011
WO    WO 2014/100719 A2    6/2014

OTHER PUBLICATIONS

Swarbrick et al., eds., Encylopedia of Pharmaceutical Technology, 13 (Marcel Decker, NY 1996), pp. 453-499.
Pearce et al, "Failure modes in anticancer drug discovery & development, Cancer Drug . . . ," Edited by Stephen Neidle, Chapter 18, pp. 424-435, Elsevier, The Netherlands (2008).
Gura, "Systems for Identifying New Drugs Are Often Faulty," Cancer Models, Science 278(5340): 1041-1042, AAAS, The United States (Nov. 1997).
Johnson et al. "Relationships between drug activity in NCI preclinical in vitro and in vivo . . . ," British J. Canc. 84(10): 1424-1431, Cancer Res. Campaign, England (2001).
Simone, Oncology: Introduction, Cecil Textbook of Medicine, 20th Ed., vol. 1, pp. 1004-1010, W.B. Saunders Company, United States (1996).
Liu, Rong, Ed., "Water-Insoluble Drug Formulation," CRC Press, 2008, Chapter 15, pp. 417-435.
Bastin et al., "Salt Selection and Optimisation Procedures for Pharmaceutical New Chemical Entities," Organic Process Research & Development, 2000, vol. 4, pp. 427-435.
Morris et al., "An Integrated Approach to the Selection of Optimal Salt form for a New Drug Candidate," International Journal of Pharmaceuticals, 105 (1994), pp. 209-217.
Adeyeye, Moji, ed., "Preformulation in Solid Dosage Form Development," Informa Healthcare, 2008, Chaper 2,3, pp. 63-80.
Gould, International Journal of Therapeutics, 33, 201 (1986).
Serajuddin, "Salt Formation to Improve Drug Solvability," Advanced Drug Delivery Reviews, vol. 59, 2007, pp. 603-615.

*Primary Examiner* — Deepak R Rao
(74) *Attorney, Agent, or Firm* — Duke M. Fitch; Kathryn A. Lutomski; Edward R. Gimmi (57) ABSTRACT

Disclosed are novel crystalline salts of (S)-6-((1-acetylpiperidin-4-yl)amino)-N-(3-(3,4-dihydroisoquinolin-2(1H)-yl)-2-hydroxypropyl)pyrimidine-4-carboxamide and pharmaceutical compositions containing the same. Also disclosed are processes for the preparation thereof and methods for use thereof.

15 Claims, 6 Drawing Sheets

CRYSTALLINE SALTS OF (S)-6-((1-ACETYLPIPERIDIN-4-YL)AMINO)-N-(3-(3,4-DIHYDROISOQUINOLIN-2(1H)-YL)-2-HYDROXYPROPYL)PYRIMIDINE-4-CARBOXAMIDE

BACKGROUND OF THE INVENTION

In the pursuit of a developable form of a solid, orally-administered pharmaceutical compound, a number of specific features are sought. Although an amorphous form of a pharmaceutical compound may be developed, compounds having high crystallinity are generally preferred. Often such highly crystalline compounds are salts.

International Patent Application Number PCT/US2013/77235 describes a series of compounds which are indicated as inhibitors of protein arginine methyltransferase 5 (PRMT5), and which are indicated as being useful in the treatment of PRMT5-mediated disorders. Specifically disclosed in that application is the compound (S)-6-((1-acetylpiperidin-4-yl)amino)-N-(3-(3,4-dihydroisoquinolin-2(1H)-yl)-2-hydroxypropyl)pyrimidine-4-carboxamide (hereinafter "Compound A"). Identification of a stable, crystalline form of such compound with suitable properties for oral administration would be highly desirable for the treatment of PRMT5-mediated diseases.

SUMMARY OF THE INVENTION

The present invention relates to novel crystalline salts of (S)-6-((1-acetylpiperidin-4-yl)amino)-N-(3-(3,4-dihydroisoquinolin-2(1H)-yl)-2-hydroxypropyl)pyrimidine-4-carboxamide, in particular the succinate salt (hereinafter "Compound B") and the benzoate salt (hereinafter "Compound C"). The compounds of the invention are represented by Formula (I):

(I)

wherein X is succinic acid or benzoic acid.

The compounds of this invention are useful for inhibiting protein arginine methyltransferase 5 (PRMT5), and for treating proliferative diseases such as cancer, in particular hematopoietic cancer, lung cancer, prostate cancer, melanoma, and pancreatic cancer.

DETAILED DESCRIPTION OF THE INVENTION

The present invention is directed to salts of (S)-6-((1-acetylpiperidin-4-yl)amino)-N-(3-(3,4-dihydroisoquinolin-2(1H)-yl)-2-hydroxypropyl)pyrimidine-4-carboxamide, in particular the succinate salt (hereinafter "Compound B") and the benzoate salt (hereinafter "Compound C").

In some embodiments, a crystalline form of the succinate salt of (S)-6-((1-acetylpiperidin-4-yl)amino)-N-(3-(3,4-dihydroisoquinolin-2(1H)-yl)-2-hydroxypropyl)pyrimidine-4-carboxamide (Compound B—Form 1) is characterized by an X-ray powder diffraction (XRPD) pattern comprising at least nine diffraction angles, when measured using Cu $K_\alpha$ radiation, selected from a group consisting of about 4.5, 8.2, 9.0, 10.4, 13.5, 15.8, 16.4, 17.3, 17.7, 18.1, 18.8, 19.6, 20.8, 21.9, 22.7, 23.3, 24.0, 24.7, 26.4, 28.2, and 29.6 degrees 2θ. In another embodiment, Compound B—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 4.5, 8.2, 9.0, 10.4, 13.5, 15.8, 16.4, 17.3, 17.7, 18.1, 18.8, 19.6, 20.8, 21.9, 22.7, 23.3, 24.0, 24.7, 26.4, 28.2, and 29.6 degrees 2θ. In another embodiment, Compound B—Form 1 is characterized by an X-ray powder diffraction (XRPD) pattern comprising at least three diffraction angles, when measured using Cu $K_\alpha$ radiation, selected from a group consisting of about 4.5, 8.2, 9.0, 10.4, 13.5, 15.8, 16.4, 17.3, 17.7, 18.1, 18.8, 19.6, 20.8, 21.9, 22.7, 23.3, 24.0, 24.7, 26.4, 28.2, and 29.6 degrees 2θ.

In another embodiment, Compound B—Form 1 is characterized by an X-ray powder diffraction (XRPD) pattern comprising at least nine diffraction angles, when measured using Cu $K_\alpha$ radiation, selected from a group consisting of about 4.5, 8.2, 10.4, 13.5, 15.8, 16.4, 17.3, 17.7, 18.1, 18.8, 19.6, 20.8, 21.9, 23.3, and 24.0 degrees 2θ. In another embodiment, Compound B—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 4.5, 8.2, 10.4, 13.5, 15.8, 16.4, 17.3, 17.7, 18.1, 18.8, 19.6, 20.8, 21.9, 23.3, and 24.0 degrees 2θ. In another embodiment, Compound B—Form 1 is characterized by an X-ray powder diffraction (XRPD) pattern comprising at least three diffraction angles, when measured using Cu $K_\alpha$ radiation, selected from a group consisting of about 4.5, 8.2, 10.4, 13.5, 15.8, 16.4, 17.3, 17.7, 18.1, 18.8, 19.6, 20.8, 21.9, 23.3, and 24.0 degrees 2θ.

In another embodiment, Compound B—Form 1 is characterized by an X-ray powder diffraction (XRPD) pattern comprising at least nine diffraction angles, when measured using Cu $K_\alpha$ radiation, selected from a group consisting of about 4.5, 8.2, 10.4, 13.5, 15.8, 16.4, 17.7, 18.1, 18.8, 20.8, 21.9, 23.3, and 24.0 degrees 2θ. In another embodiment, Compound B—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 4.5, 8.2, 10.4, 13.5, 15.8, 16.4, 17.7, 18.1, 18.8, 20.8, 21.9, 23.3, and 24.0 degrees 2θ. In another embodiment, Compound B—Form 1 is characterized by an X-ray powder diffraction (XRPD)

pattern comprising at least three diffraction angles, when measured using Cu K$_\alpha$ radiation, selected from a group consisting of about 4.5, 8.2, 10.4, 13.5, 15.8, 16.4, 17.7, 18.1, 18.8, 20.8, 21.9, 23.3, and 24.0 degrees 2θ.

In still another embodiment, Compound B—Form 1 is characterized by an X-ray powder diffraction (XRPD) pattern comprising diffraction angles, when measured using Cu K$_\alpha$ radiation, of about 4.5, 10.4, 17.7, 18.1, 20.8, and 24.0 degrees 2θ. In yet another embodiment, Compound B—Form 1 is characterized by an X-ray powder diffraction (XRPD) pattern substantially in accordance with FIG. 1.

In some embodiments, a crystalline form of the benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide (Compound C—Form 1) is characterized by an X-ray powder diffraction (XRPD) pattern comprising at least nine diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 21.5, 22.1, 23.4, 24.0, 24.2, 25.1, 25.9, 27.1, 28.8, and 30.7 degrees 2θ. In another embodiment, Compound C—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 21.5, 22.1, 23.4, 24.0, 24.2, 25.1, 25.9, 27.1, 28.8, and 30.7 degrees 2θ. In another embodiment, Compound C—Form 1 is characterized by an X-ray powder diffraction (XRPD) pattern comprising at least three diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 21.5, 22.1, 23.4, 24.0, 24.2, 25.1, 25.9, 27.1, 28.8, and 30.7 degrees 2θ.

In another embodiment, Compound C—Form 1 is characterized by an X-ray powder diffraction (XRPD) pattern comprising at least nine diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 22.1, 24.0, 24.2, 25.9, 27.1, and 28.8 degrees 2θ. In another embodiment, Compound C—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 22.1, 24.0, 24.2, 25.9, 27.1, and 28.8 degrees 2θ. In another embodiment, Compound C—Form 1 is characterized by an X-ray powder diffraction (XRPD) pattern comprising at least three diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 22.1, 24.0, 24.2, 25.9, 27.1, and 28.8 degrees 2θ.

In another embodiment, Compound C—Form 1 is characterized by an X-ray powder diffraction (XRPD) pattern comprising at least nine diffraction angles, when measured using Cu K$_\alpha$ radiation, selected from a group consisting of about 4.3, 7.7, 15.6, 16.6, 16.9, 18.1, 18.6, 22.1, 24.0, 27.1, and 28.8 degrees 2θ. In another embodiment, Compound C—Form 1 is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 4.3, 7.7, 15.6, 16.6, 16.9, 18.1, 18.6, 22.1, 24.0, 27.1, and 28.8 degrees 2θ. In another embodiment, Compound C—Form 1 is characterized by an X-ray powder diffraction (XRPD) pattern comprising at least three diffraction angles, when measured using Cu K$_\alpha$ radiation, selected from a group consisting of about 4.3, 7.7, 15.6, 16.6, 16.9, 18.1, 18.6, 22.1, 24.0, 27.1, and 28.8 degrees 2θ.

In still another embodiment, Compound C—Form 1 is characterized by an X-ray powder diffraction (XRPD) pattern comprising diffraction angles, when measured using Cu K$_\alpha$ radiation, of about 4.3, 7.7, 18.1, 18.6, 22.1, and 24.0 degrees 2θ. In yet another embodiment, Compound C—Form 1 is characterized by an X-ray powder diffraction (XRPD) pattern substantially in accordance with FIG. 2.

Figure 3:
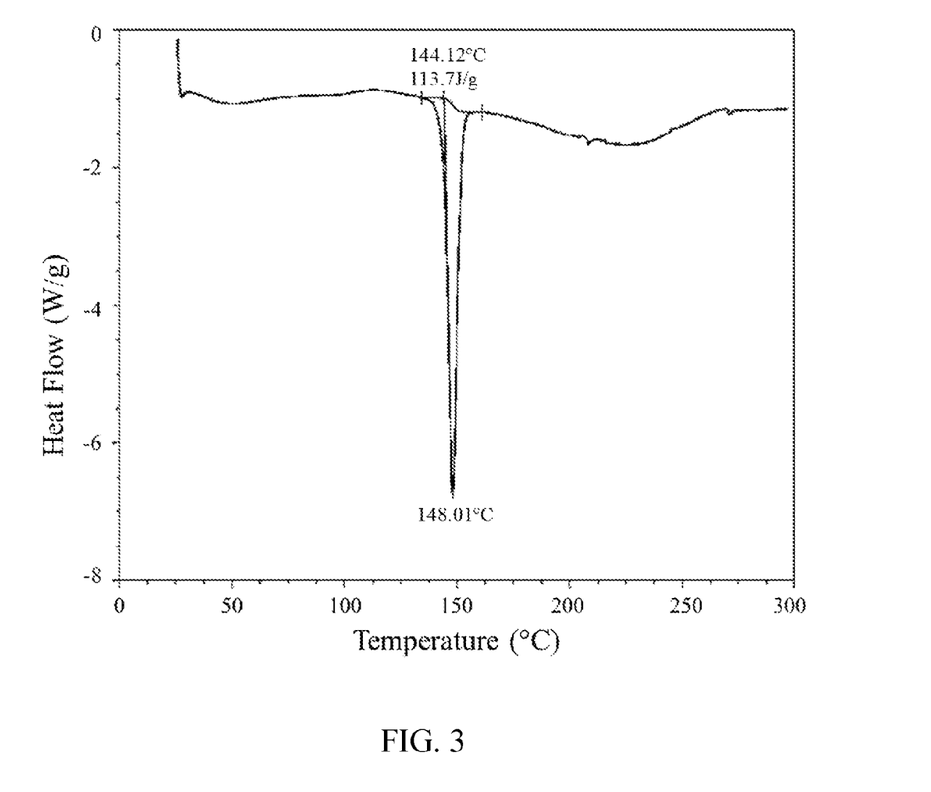
FIG. 3 shows a differential scanning calorimetry trace of Compound B—Form 1.
Figure 5:
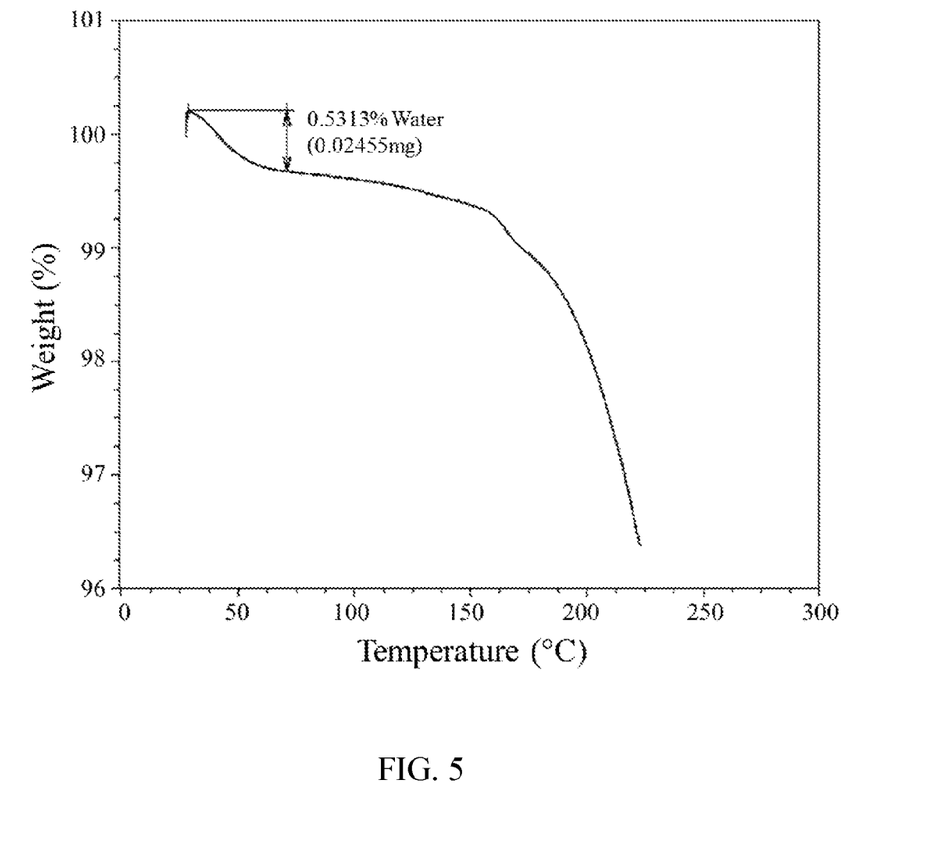
FIG. 5 shows a thermogravimetric analysis trace of Compound B—Form 1.

In further embodiments, Compound B—Form 1 is characterized by a differential scanning calorimetry trace substantially in accordance with FIG. 3 and/or a thermogravimetric analysis trace substantially in accordance with FIG. 5.

Figure 4:
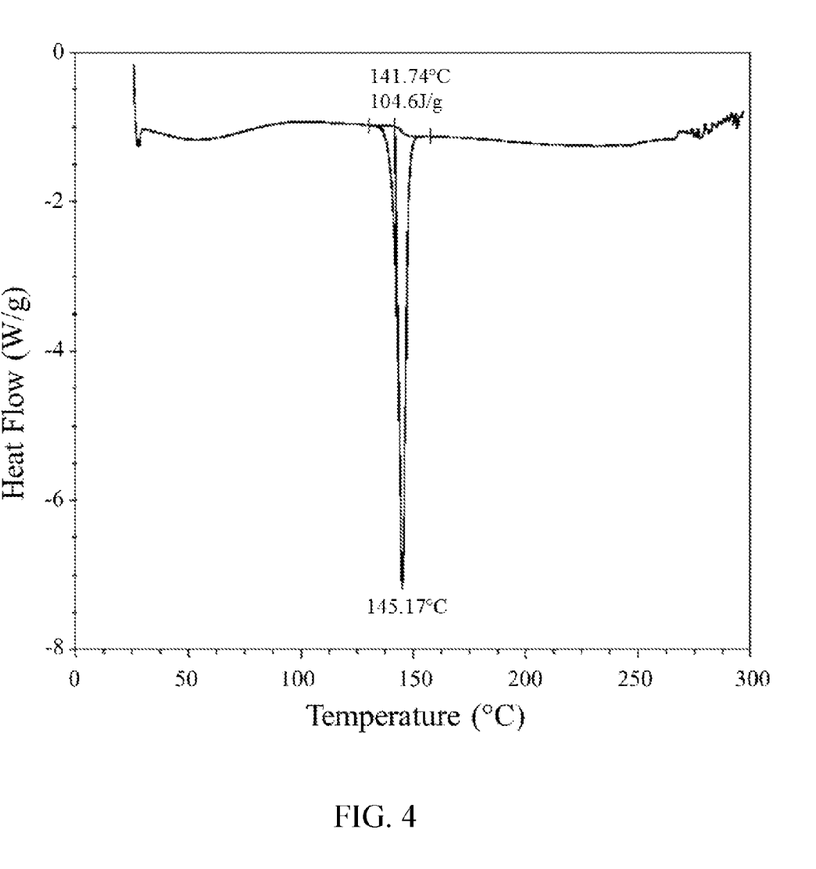
FIG. 4 shows a differential scanning calorimetry trace of Compound C—Form 1.
Figure 6:
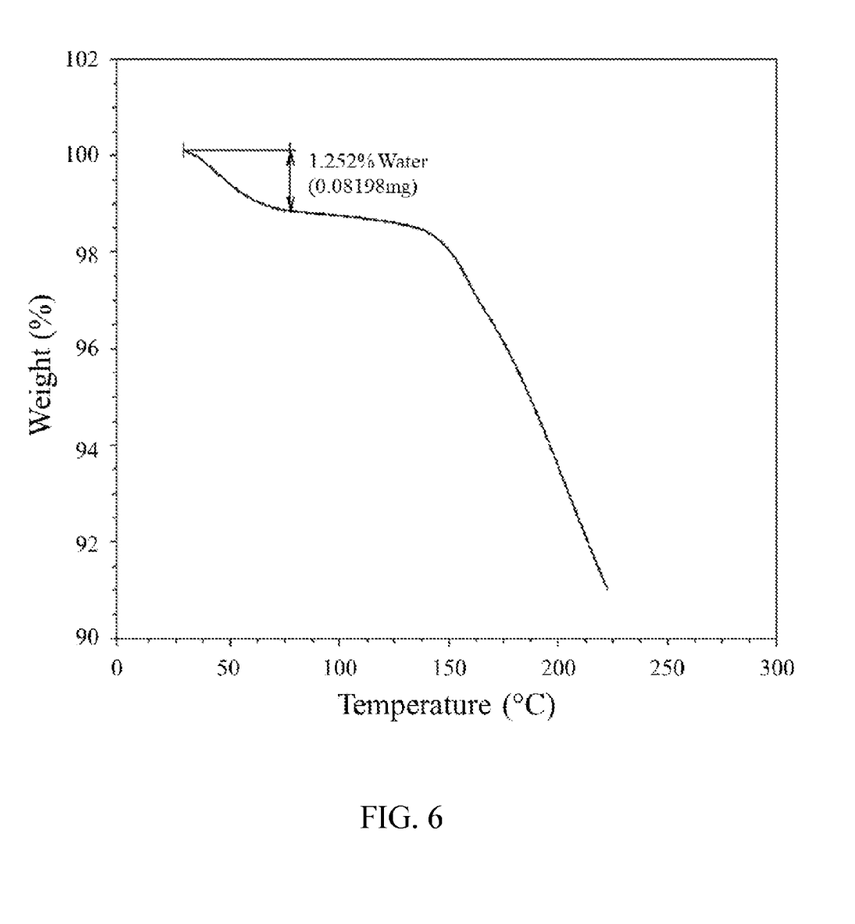
FIG. 6 shows a thermogravimetric analysis trace of Compound C—Form 1.

In further embodiments, Compound C—Form 1 is characterized by a differential scanning calorimetry trace substantially in accordance with FIG. 4 and/or a thermogravimetric analysis trace substantially in accordance with FIG. 6.

In still further embodiments, as a person having ordinary skill in the art will understand, Compound B—Form 1 is characterized by any combination of the analytical data characterizing the aforementioned embodiments. For example, in one embodiment, Compound B—Form 1 is characterized by an X-ray powder diffraction (XRPD) pattern substantially in accordance with FIG. 1 and a differential scanning calorimetry trace substantially in accordance with FIG. 3 and a thermogravimetric analysis trace substantially in accordance with FIG. 5. In another embodiment, Compound B—Form 1 is characterized by an X-ray powder diffraction (XRPD) pattern substantially in accordance with FIG. 1 and a differential scanning calorimetry trace substantially in accordance with FIG. 3. In another embodiment, Compound B—Form 1 is characterized by an X-ray powder diffraction (XRPD) pattern substantially in accordance with FIG. 1 and a thermogravimetric analysis trace substantially in accordance with FIG. 5. In another embodiment, Compound B—Form 1 is characterized by an X-ray powder diffraction (XRPD) pattern comprising diffraction angles, when measured using Cu K$_\alpha$ radiation, of about 4.5, 10.4, 17.7, 18.1, 20.8, and 24.0 degrees 2θ, and a differential scanning calorimetry trace substantially in accordance with FIG. 3. In another embodiment, Compound B—Form 1 is characterized by an X-ray powder diffraction (XRPD) pattern comprising diffraction angles, when measured using Cu K$_\alpha$ radiation, of about 4.5, 10.4, 17.7, 18.1, 20.8, and 24.0 degrees 2θ, and a thermogravimetric analysis trace substantially in accordance with FIG. 5.

In still further embodiments, as a person having ordinary skill in the art will understand, Compound C—Form 1 is characterized by any combination of the analytical data characterizing the aforementioned embodiments. For example, in one embodiment, Compound C—Form 1 is characterized by an X-ray powder diffraction (XRPD) pattern substantially in accordance with FIG. 2 and a differential scanning calorimetry trace substantially in accordance with FIG. 4 and a thermogravimetric analysis trace substantially in accordance with FIG. 6. In another embodiment, Compound C—Form 1 is characterized by an X-ray powder diffraction (XRPD) pattern substantially in accordance with FIG. 2 and a differential scanning calorimetry trace substantially in accordance with FIG. 4. In another embodiment, Compound C—Form 1 is characterized by an X-ray powder diffraction (XRPD) pattern substantially in accordance with FIG. 2 and a thermogravimetric analysis trace substantially in accordance with FIG. 6. In another embodiment, Compound C—Form 1 is characterized by an X-ray powder diffraction (XRPD) pattern comprising diffraction angles, when measured using Cu K$_\alpha$ radiation, of about 4.3, 7.7, 18.1, 18.6, 22.1, and 24.0 degrees 2θ, and a differential scanning calorimetry trace substantially in accordance with FIG. 4. In another embodiment, Compound C—Form 1 is characterized by an X-ray powder diffraction (XRPD) pattern comprising diffraction angles, when measured using Cu K$_\alpha$ radiation, of about 4.3, 7.7, 18.1, 18.6, 22.1, and 24.0 degrees 2θ, and a thermogravimetric analysis trace substantially in accordance with FIG. 6.

Figure 1:
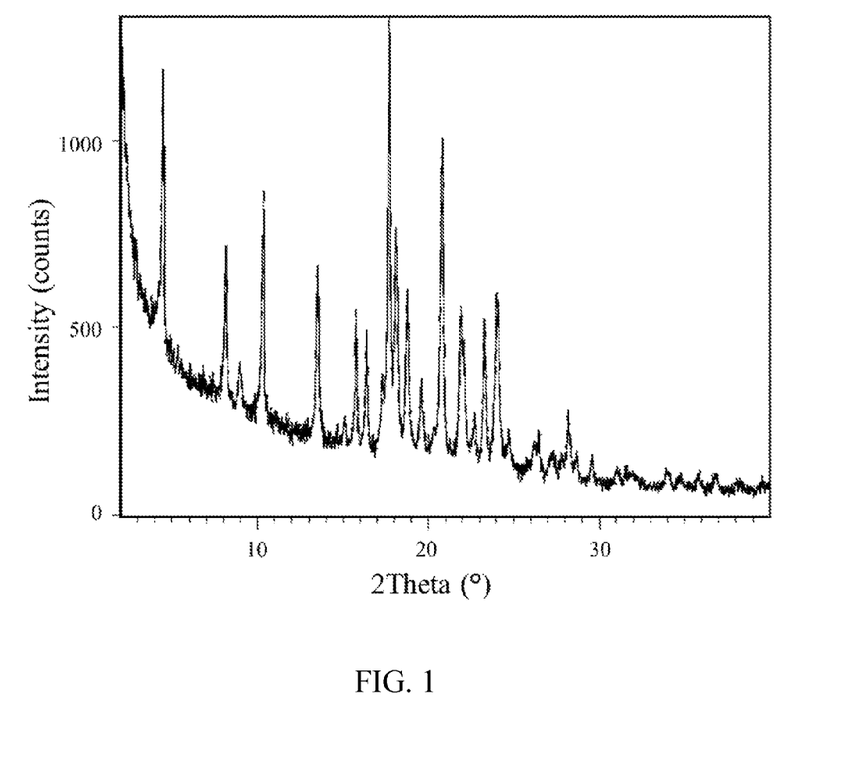
FIG. 1 shows an X-ray powder diffraction pattern of Compound B—Form 1.
Figure 2:
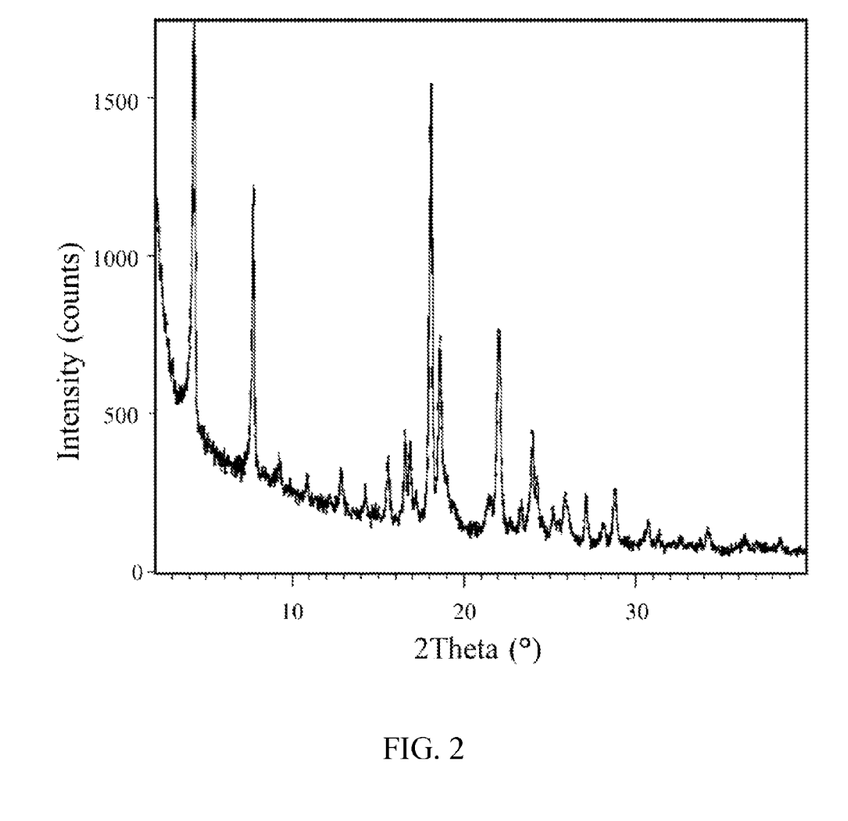
FIG. 2 shows an X-ray powder diffraction pattern of Compound C—Form 1.

An XRPD pattern will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 or 2 provided herein is an XRPD pattern that would be considered by one skilled in the art to represent a compound possessing the same crystal form as the compound that provided the XRPD pattern of FIG. 1 or 2. That is, the XRPD pattern may be identical to that of FIG. 1 or 2, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of the succinate salt of (S)-6-((1-acetylpiperidin-4-yl)amino)-N-(3-(3,4-dihydroisoquinolin-2(1H)-yl)-2-hydroxypropyl)pyrimidine-4-carboxamide, with FIG. 1 and, using expertise and knowledge in the art, readily determine whether the XRPD pattern of the sample is substantially in accordance with the XRPD pattern of Compound B—Form 1. If the XRPD pattern is substantially in accordance with FIG. 1, the sample form can be readily and accurately identified as having the same form as Compound B—Form 1. Similarly, if an XRPD pattern of a sample of the benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide is substantially in accordance with FIG. 2, the sample form can be readily and accurately identified as having the same form as Compound C—Form 1.

"Compounds of the invention" means the succinate salt and benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide, and in some embodiments, specifically the crystalline form defined herein as Compound B—Form 1, or in some embodiments, specifically the crystalline form defined herein as Compound C—Form 1.

The invention includes a therapeutic method for treating or ameliorating a PRMT5-mediated disorder in a human in need thereof comprising administering to a human in need thereof an effective amount of a compound of the invention or a composition comprising an effective amount of a compound of the invention and an optional pharmaceutically acceptable carrier. In certain embodiments, the PRMT5-mediated disorder is a proliferative disorder, a metabolic disorder, or a blood disorder. In certain embodiments, compounds described herein are useful for treating cancer. In certain embodiments, the inhibition of PRMT5 by a compound of the invention is useful in treating the following non-limiting list of cancers: breast cancer, esophageal cancer, bladder cancer, lung cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenocarcinoma. In certain embodiments, compounds described herein are useful for treating hematopoietic cancer, lung cancer, prostate cancer, melanoma, or pancreatic cancer. In certain embodiments, compounds described herein are useful for treating a hemoglobinopathy. In certain embodiments, compounds described herein are useful for treating sickle cell anemia. In certain embodiments, compounds described herein are useful for treating diabetes or obesity.

As used herein, the term "PRMT5-mediated disorder" means any disease, disorder, or other pathological condition in which PRMT5 is known to play a role. Accordingly, in some embodiments, the present disclosure relates to treating or lessening the severity of one or more diseases in which PRMT5 is known to play a role.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a compound of the invention is useful in treating a metabolic disorder, such as diabetes or obesity. In some embodiments, a compound of the invention is useful to delay the onset of, slow the progression of, or ameliorate the symptoms of, diabetes. In some embodiments, the diabetes is Type 1 diabetes. In some embodiments, the diabetes is Type 2 diabetes. In some embodiments, a compound of the invention is useful to delay the onset of, slow the progression of, or ameliorate the symptoms of, obesity. In some embodiments, a compound of the invention is useful to make a subject lose weight. In some embodiments, a compound of the invention could be used in combination with other compounds, drugs, or therapeutics, such as metformin and insulin, to treat diabetes and/or obesity.

In some embodiments, a compound of the invention is useful in treating a blood disorder, e.g., a hemoglobinopathy, such as sickle cell disease or β-thalassemia. In some embodiments, a compound of the invention is useful to delay the onset of, slow the progression of, or ameliorate the symptoms of, sickle cell disease. In some embodiments, a compound of the invention is useful to delay the onset of, slow the progression of, or ameliorate the symptoms of, β-thalassemia. In some embodiments, a compound of the invention could be used in combination with other compounds, drugs, or therapeutics, to treat a hemoglobinopathy such as sickle cell disease or β-thalassemia.

As used herein, "treatment" in reference to a condition means: (1) the amelioration of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated.

"Effective amount" means that amount of drug substance (i.e. a compound of the present invention) that elicits the desired biological response in a subject. Such response includes alleviation of the symptoms of the disease or disorder being treated. The effective amount of a compound of the invention in such a therapeutic method is about 0.001 to 100 mg per kg patient body weight per day which can be administered in single or multiple doses. In some embodiments, the dosage level will be about 0.01 to about 25 mg/kg per day. In some embodiments, the dosage level will be about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compound may be administered on a regimen of 1 to 4 times per day, preferably once or twice per day. In some embodiments, a compound described herein is administered one or more times per day, for multiple days. In some embodiments, the dosing regimen is continued for days, weeks, months, or years.

It is to be understood, however, that the specific dose level and frequency of dosage for any particular patient may be varied and will depend upon a variety of factors including age, body weight, hereditary characteristics, general health, gender, diet, mode and time of administration, rate of excretion, drug combination, and the nature and severity of the particular condition being treated.

Administration methods include administering an effective amount of a compound or composition of the invention at different times during the course of therapy or concurrently in a combination form. The methods of the invention include all known therapeutic treatment regimens.

The compounds and compositions of the present invention can be combined with other compounds and compositions having related utilities to prevent and treat the condition or disease of interest, such as a proliferative disorder, a metabolic disorder, or a blood disorder. Selection of the appropriate agents for use in combination therapies can be made by one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

Combination therapy includes co-administration of the compound of the invention and said other agent, sequential administration of the compound of the invention and the other agent, administration of a composition containing the compound of the invention and the other agent, or simultaneous administration of separate compositions containing the compound of the invention and the other agent.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

The invention further includes the use of a compound of the invention as an active therapeutic substance, in particular in the treatment of PRMT5-mediated disorders. In particular, the invention includes the use of a compound of the invention in the treatment of a proliferative disorder, a metabolic disorder, or a blood disorder.

In another aspect, the invention includes the use of compounds of the invention in the manufacture of a medicament for use in the treatment of the above disorders.

The present invention is also directed to a pharmaceutical composition comprising a compound of the invention and a pharmaceutically acceptable carrier. The present invention is further directed to a method of preparing a pharmaceutical composition comprising admixing a compound of the invention and a pharmaceutically acceptable carrier.

"Pharmaceutically acceptable carrier" means any one or more compounds and/or compositions that are of sufficient purity and quality for use in the formulation of the compound of the invention that, when appropriately administered to a human, do not produce an adverse reaction, and that are used as a vehicle for a drug substance (i.e. a compound of the present invention). Carriers may include excipients, diluents, granulating and/or dispersing agents, surface active agents and/or emulsifiers, binding agents, preservatives, buffering agents, lubricating agents, and natural oils.

The invention further includes the process for making the composition comprising mixing a compound of the invention and an optional pharmaceutically acceptable carrier; and includes those compositions resulting from such a process, which process includes conventional pharmaceutical techniques. For example, a compound of the invention may be nanomilled prior to formulation. A compound of the invention may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders.

The oral composition is preferably formulated as a homogeneous composition, wherein the drug substance (i.e. a compound of the present invention) is dispersed evenly throughout the mixture, which may be readily subdivided into dosage units containing equal amounts of the compound of the invention. Preferably, the compositions are prepared by mixing a compound of the invention with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste); gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

A compound of the invention may also be administered via a delayed release composition, wherein the composition includes a compound of the invention and a biodegradable slow release carrier (e.g. a polymeric carrier) or a pharmaceutically acceptable non-biodegradable slow release carrier (e.g. an ion exchange carrier).

Biodegradable and non-biodegradable delayed release carriers are well known in the art. Biodegradable carriers are used to form particles or matrices which retain a drug substance(s) (i.e. a compound of the present invention) and which slowly degrade/dissolve in a suitable environment (e.g. aqueous, acidic, basic and the like) to release the drug substance(s). Such particles degrade/dissolve in body fluids to release the drug substance(s) (i.e. compounds of the present invention) therein. The particles are preferably nanoparticles (e.g. in the range of about 1 to 500 nm in diameter, preferably about 50-200 nm in diameter, and most preferably about 100 nm in diameter). In a process for preparing a slow release composition, a slow release carrier and the compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

In certain embodiments, this invention relates to a pharmaceutical composition comprising Compound B. In another embodiment, this invention relates to a pharmaceutical composition comprising Compound B wherein at least 10% by weight of Compound B is present as Compound B—Form 1. In another embodiment, this invention relates to a pharmaceutical composition comprising Compound B wherein at least 20% by weight, or at least 30% by weight, or at least 40% by weight, or at least 50% by weight, or at least 60% by weight, or at least 70% by weight, or at least 80% by weight, or at least 90% by weight of Compound B is present as Compound B—Form 1. In another embodiment, this invention relates to a pharmaceutical composition comprising Compound B wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound B is present as Compound B—Form 1.

In another embodiment, this invention relates to a pharmaceutical composition comprising Compound B wherein not more than 90% by weight of Compound B is amorphous. In another embodiment, this invention relates to a pharmaceutical composition comprising Compound B wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of Compound B is amorphous. In another embodiment, this invention relates to a pharmaceutical composition comprising Compound B wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of Compound B is amorphous.

In another embodiment, this invention relates to a pharmaceutical composition comprising Compound B wherein not more than 90% by weight of Compound B is present in a form other than Compound B—Form 1. In another embodiment, this invention relates to a pharmaceutical composition comprising Compound B wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of Compound B is present in a form other than Compound B—Form 1. In another embodiment, this invention relates to a pharmaceutical composition comprising Compound B wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of Compound B is present in a form other than Compound B—Form 1.

In certain embodiments, this invention relates to a pharmaceutical composition comprising Compound C. In another embodiment, this invention relates to a pharmaceutical composition comprising Compound C wherein at least 10% by weight of Compound C is present as Compound C—Form 1. In another embodiment, this invention relates to a pharmaceutical composition comprising Compound C wherein at least 20% by weight, or at least 30% by weight, or at least 40% by weight, or at least 50% by weight, or at least 60% by weight, or at least 70% by weight, or at least 80% by weight, or at least 90% by weight of Compound C is present as Compound C—Form 1. In another embodiment, this invention relates to a pharmaceutical composition comprising Compound C wherein at least 95% by weight, or at least 96% by weight, or at least 97% by weight, or at least 98% by weight, or at least 99% by weight, or at least 99.5% by weight, or at least 99.8% by weight, or at least 99.9% by weight of Compound C is present as Compound C—Form 1.

In another embodiment, this invention relates to a pharmaceutical composition comprising Compound C wherein not more than 90% by weight of Compound C is amorphous. In another embodiment, this invention relates to a pharmaceutical composition comprising Compound C wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of Compound C is amorphous. In another embodiment, this invention relates to a pharmaceutical composition comprising Compound C wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of Compound C is amorphous.

In another embodiment, this invention relates to a pharmaceutical composition comprising Compound C wherein not more than 90% by weight of Compound C is present in a form other than Compound C—Form 1. In another embodiment, this invention relates to a pharmaceutical composition comprising Compound C wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of Compound C is present in a form other than Compound C—Form 1. In another embodiment, this invention relates to a pharmaceutical composition comprising Compound C wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of Compound C is present in a form other than Compound C—Form 1.

Without further elaboration, it is believed that one skilled in the art can, using the preceding description, utilize the present invention to its fullest extent. The following Examples are, therefore, to be construed as merely illustrative and not a limitation of the scope of the present invention in any way.

Example 1

Preparation of (S)-6-((1-acetylpiperidin-4-yl)amino)-N-(3-(3,4-dihydroisoquinolin-2(1H)-yl)-2-hydroxypropyl)pyrimidine-4-carboxamide (Compound A)

(a) tert-butyl (1-acetylpiperidin-4-yl)carbamate

To a solution of tert-butyl piperidin-4-ylcarbamate (200 g, 1 mol) and triethylamine (150 g, 1.5 mol) in dichloromethane (3000 mL) was added acetic anhydride (102 g, 1 mol) dropwise over 1 hour, while maintained the temperature at 0° C. After addition, the mixture was stirred 0° C. for another 2 hours, at which time TLC showed the reaction was completed. The solution was quenched by addition of water (1 L). The organic phase was collected and washed with saturated aqueous sodium bicarbonate (1 L), dried over sodium sulfate and concentrated to give crude product. Four batches were run in parallel and produced a combined crude product weight of 670 g. LCMS (m/z): 243.1 (M+1).

(b) 1-(4-aminopiperidin-1-yl)ethanone hydrochloride

To a solution of tert-butyl (1-acetylpiperidin-4-yl)carbamate (330 g, 1.36 mol) in methanol (1000 mL) was added hydrochloric acid (4M in methanol, 300 mL) over 30 minutes to maintain the temperature at 0° C. After addition, the mixture was stirred at 0° C. for another 2 hours and then concentrated to give the crude product. Two batches were run in parallel and produced a combined crude product weight of 310 g. $^1$H NMR (400 MHz, D$_2$O) δ 4.35 (dd, J=2.0, 12.0 Hz, 1H), 3.98-3.85 (m, 1H), 3.44-3.30 (m, 1H), 3.18-3.05 (m, 1H), 2.75-2.58 (m, 1H), 2.06-1.92 (m, 5H), 1.61-1.31 (m, 2H); LCMS (m/z): 143.1 (M+1).

(c) 6-hydroxypyrimidine-4-carboxylic acid

To a solution of sodium (Z)-1,4-diethoxy-1,4-dioxobut-2-en-2-olate (55.0 g, 262 mmol) in water (500 mL) was added formamidine acetate (27.3 g, 262 mmol) and sodium hydroxide (10.5 g). After addition, the resulting mixture was stirred at 25° C. for 16 hours then concentrated and then acidified by added aqueous hydrochloric acid (1N) until pH=1. The resulting solid was collected by filtration, washed with water and ether to give 6-hydroxypyrimidine-4-carboxylic acid (6.0 g, yield: 16.3%). $^1$H NMR (400 MHz, DMSO-d$_6$) δ 12.89 (s, 1H), 8.24 (s, 1H), 6.83 (s, 1H).

(d) 6-chloropyrimidine-4-carbonyl chloride

To a stirred mixture of 6-hydroxypyrimidine-4-carboxylic acid (300 g, 2.14 mol) in ethyl acetate (3000 mL), oxalyl chloride (1356 g, 10.68 mol) was dropped slowly to maintain a reaction temperature below 30° C. After addition, the mixture was stirred at 20° C. for 30 minutes and then 2 mL of N,N-dimethylformamide was added to the mixture. The mixture was then stirred at 80° C. for 16 hours and concentrated to give the crude product as black solid. Three batches were run in parallel and produced a combined crude product weight of 787 g.

(e) (R)-2-(oxiran-2-ylmethyl)-1,2,3,4-tetrahydroisoquinoline

To a solution of 1,2,3,4-tetrahydroisoquinoline (10 g, 0.15 mol) in tetrahydrofuran (100 mL) at 0° C. was added potassium fluoride (22 g, 0.3 mmol). After 1 hour, (S)-oxiran-2-ylmethyl 3-nitrobenzenesulfonate (21.4 g, 0.17 mmol) was added and the resulting solution was stirred at 22° C. for 16 hours. The solid was removed by filtration and washed with tetrahydrofuran. The solution was then concentrated (15 g, Yield 53%). LCMS (m/z): 190.1 (M+1).

(f) (S)-1-amino-3-(3,4-dihydroisoquinolin-2(1H)-yl)propan-2-ol

To a solution of (R)-2-(oxiran-2-ylmethyl)-1,2,3,4-tetrahydroisoquinoline (15 g, 0.08 mol) in ethanol (100 mL) at −78° C. was slowly bubbled ammonia gas. The reaction mixture was then sealed and heated at 80° C. for 3 hours. The reaction mixture was then concentrated (15 g, Yield 92%). LCMS (m/z): 207.1 (M+1).

(g) (S)-6-chloro-N-(3-(3,4-dihydroisoquinolin-2(1H)-yl)-2-hydroxypropyl)pyrimidine-4-carboxamide To a stirred mixture of (S)-1-amino-3-(3,4-dihydroisoquinolin-2(1H)-yl)propan-2-ol (247 g, 1.20 mol), and triethylamine (250 g, 2.5 mol) in dichloromethane (3500 mL) was added 6-chloropyrimidine-4-carbonyl chloride (190 g in 100 mL of dichloromethane) slowly at −60° C. over 1 hour. After addition, the mixture was then allowed to warm to 10° C. Stirring was continued for 1 hour, at which time TLC showed the reaction was completed. The reaction was quenched by addition of water (1.5 L). The organic phase was collected, dried over sodium sulfate and evaporated. The residue was purified by flash chromatography (ethyl acetate~dichloromethane:methanol=10:1) to give the desired product as a pale yellow solid. Four batches were run in parallel and produced a combined crude product weight of 800 g, 49% yield. $^1$H NMR (400 MHz, MeOD-d$_4$) δ 8.73 (d, J=1.0 Hz, 1H), 8.07 (d, J=1.0 Hz, 1H), 7.17-7.06 (m, 3H), 7.00 (d, J=7.0 Hz, 1H), 4.12 (q, J=6.0 Hz, 1H), 3.74 (s, 2H), 3.64-3.53 (m, 2H), 2.94 (q, J=5.5 Hz, 2H), 2.92-2.81 (m, 2H), 2.78-2.64 (m, 2H); LCMS (m/z): 347.2 [M+H]$^+$.

(h) (S)-6-((1-acetylpiperidin-4-yl)amino)-N-(3-(3,4-dihydroisoquinolin-2(1H)-yl)-2-hydroxypropyl)pyrimidine-4-carboxamide A solution of (S)-6-chloro-N-(3-(3,4-dihydroisoquinolin-2(1H)-yl)-2-hydroxypropyl)pyrimidine-4-carboxamide (190 g, 0.55 mmol), 1-(4-aminopiperidin-1-yl)ethanone (78 g), and triethylamine (100 g, 1 mol) in isopropanol (2000 mL) was stirred at 60° C. for 16 hours. The mixture was concentrated and the residue was purified by flash chromatography to give the desired product. Four batches were run in parallel and produced a combined crude product weight of 482 g. This material was further purified by preparative HPLC to give the title compound (325 g, >98% purity, free base form). $^1$H NMR (400 MHz, MeOD-d$_4$) δ 8.26 (s, 1H), 7.15-7.02 (m, 5H), 4.46 (m, 1H), 4.15-4.07 (m, 2H), 3.88 (m, 1H), 3.74 (s, 2H), 3.53 (m, 2H), 3.33 (m, 1H), 2.95-2.86 (m, 5H), 2.68 (m, 2H), 2.14-2.01 (m, 5H), 1.48-1.42 (m, 2H); LCMS (m/z): 453.3 [M+H]$^+$.

Example 2

Preparation of

The succinate salt of (S)-6-((1-acetylpiperidin-4-yl) amino)-N-(3-(3,4-dihydroisoquinolin-2(1H)-yl)-2-hydroxypropyl)pyrimidine-4-carboxamide (Compound B)

(a) Small Scale
Ethyl acetate (0.5 mL) was added to (S)-6-((1-acetylpiperidin-4-yl)amino)-N-(3-(3,4-dihydroisoquinolin-2(1H)-yl)-2-hydroxypropyl)pyrimidine-4-carboxamide (amorphous free-base) (19.9 mg). To the suspension succinic acid (1M solution in methanol, 1.0 equivalent) was added and the temperature of the suspension was cycled between 40° C. and 5° C. for 48 hours. The crystalline salt was isolated by centrifuge filtration and the solids were analyzed by XRPD.
(b) Large Scale
Isopropanol (5.0 mL) was added to (S)-6-((1-acetylpiperidin-4-yl)amino)-N-(3-(3,4-dihydroisoquinolin-2(1H)-yl)-2-hydroxypropyl)pyrimidine-4-carboxamide (amorphous free-base) (361.3 mg). The suspension was heated to 40° C. and succinic acid (1M solution in methanol, 1.0 equivalent) was added. To the suspension, seeds of succinate salt (prepared according to procedure (a) above) were added and the temperature of the suspension was cycled between 40° C. and 5° C. for 16 hours. The crystalline succinate salt was isolated under vacuum, air-dried for 15 minutes and dried in a vacuum oven at 40° C. for 4 hours. The yield of the crystalline succinate salt was 68.6% (312.9 mg). Stoichiometry of the succinate salt was determined to be approximately 1:1 ((S)-6-((1-acetylpiperidin-4-yl)amino)-N-(3-(3,4-dihydroisoquinolin-2(1H)-yl)-2-hydroxypropyl) pyrimidine-4-carboxamide:succinic acid) by $^1$H NMR.

The X-ray powder diffraction (XRPD) pattern of this material (Compound B—Form 1) is shown in FIG. 1 and a summary of the diffraction angles and d-spacings is given in Table I below. The XRPD analysis was conducted on a PANanalytical X'Pert Pro Diffractometer on Si zero-background wafers. The acquisition conditions included: Cu K$_α$ radiation, generator tension: 45 kV, generator current: 40 mA, step size: 0.02° 2θ.

TABLE I

| Diff. Angle [°2θ] | d-spacing [Å] |
|---|---|
| 4.479 | 19.7134 |
| 8.157 | 10.831 |
| 8.975 | 9.8449 |
| 10.36 | 8.5314 |
| 13.522 | 6.5428 |
| 15.096 | 5.8641 |
| 15.76 | 5.6184 |
| 16.395 | 5.4024 |
| 17.313 | 5.1178 |
| 17.699 | 5.007 |
| 18.084 | 4.9014 |
| 18.8 | 4.7164 |
| 19.618 | 4.5214 |
| 20.824 | 4.2623 |
| 21.894 | 4.0564 |
| 22.711 | 3.9122 |
| 23.297 | 3.8151 |
| 24.017 | 3.7023 |
| 24.701 | 3.6013 |
| 26.441 | 3.3682 |
| 28.176 | 3.1645 |
| 29.581 | 3.0174 |

The differential scanning calorimetry (DSC) thermogram of the title compound was recorded on a TA Instruments Q100 Differential Scanning Calorimeter equipped with an autosampler and a refrigerated cooling system under 40 mL/min N$_2$ purge and is shown in FIG. 3. The experiments were conducted using a heating rate of 15° C./min in a crimped aluminum pan. The DSC thermogram of Compound B—Form 1 exhibits an endotherm with an onset temperature at about 144.1° C. A person skilled in the art would recognize that the onset temperature of the endotherm may vary depending on the experimental conditions.

The thermogravimetric analysis (TGA) thermogram of the title compound was recorded on a TA Instruments Q5000 Thermogravimetric Analyzer and is shown in FIG. 5. The experiments were conducted with 60 mL/min N$_2$ flow and a heating rate of 15° C./min. The TGA thermogram of Compound B—Form 1 exhibits approximately 0.53% loss of water below 75° C.

Compound B demonstrated the following properties:

≤0.4% degradation after 4 weeks at 25° C./60% RH in an open vessel, 40° C./75% RH in an open vessel, and 50° C./Ambient conditions in a closed vessel. No physical changes detected by XRPD analysis after 6 weeks at 25° C./60% RH in an open vessel, 40° C./75% RH in an open vessel, and 50° C./Ambient conditions in a closed vessel. Approximately 1.4% degradation by photolysis at 1×ICH solid state with no form change observed by XRPD.

Solubility in Bio-Relevant Media and Britton-Robinson Buffer (BRB) Solutions

| Media | 24 h pH | 24 h solubility (mg/mL)$^4$ |
|---|---|---|
| Water | 5.2 | >1.8 |
| SGF$^1$ pH 1.6 | 1.7 | >1.8 |
| FaSSIF$^2$ pH 6.5 | 6.3 | >1.8 |
| FeSSIF$^3$ pH 6.5 | 6.4 | >1.8 |

| Media | 24 h pH | 24 h solubility (mg/mL)[4] |
|---|---|---|
| BRB pH 4 | 4.2 | >1.7 |
| BRB pH 7 | 6.7 | >2 |
| BRB pH 10 | 9.3 | >1.9 |

[1]Simulated Gastric Fluid
[2]Fasted State Simulated Intestinal Fluid
[3]Fed State Simulated Intestinal Fluid
[4]Unsaturated

Example 3

Preparation of

The benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide (Compound C)

(a) Small Scale

Methyl tert-butyl ether (0.5 mL) was added to (S)-6-((1-acetylpiperidin-4-yl)amino)-N-(3-(3,4-dihydroisoquinolin-2(1H)-yl)-2-hydroxypropyl)pyrimidine-4-carboxamide (amorphous free-base) (21.5 mg). To the suspension, benzoic acid (3 M solution in tetrahydrofuran, 1.0 equivalent) was added and the temperature of the suspension was cycled between 40° C. and 5° C. for 48 hours. The crystalline salt was isolated by centrifuge filtration and the solids were analyzed by XRPD.

(b) Large Scale

Isopropanol (3.5 mL) was added to (S)-6-((1-acetylpiperidin-4-yl)amino)-N-(3-(3,4-dihydroisoquinolin-2(1H)-yl)-2-hydroxypropyl)pyrimidine-4-carboxamide (amorphous free-base) (349.9 mg). The suspension was heated to 40° C. and benzoic acid (3 M solution in tetrahydrofuran, 1.0 equivalent) was added. To the suspension, seeds of benzoate salt (prepared according to procedure (a) above) were added and the temperature of the suspension was cycled between 40° C. and 5° C. for 16 hours. The crystalline benzoate salt was isolated under vacuum, air-dried for 15 minutes and dried in a vacuum oven at 40° C. for 4 hours. The yield of the crystalline benzoate salt was 68.6% (305.3 mg). Stoichiometry of the benzoate salt was determined to be approximately 1:1 ((S)-6-((1-acetylpiperidin-4-yl)amino)-N-(3-(3,4-dihydroisoquinolin-2(1H)-yl)-2-hydroxypropyl)pyrimidine-4-carboxamide:benzoic acid) by $^1$H NMR.

The X-ray powder diffraction (XRPD) pattern of this material (Compound C—Form 1) is shown in FIG. 2 and a summary of the diffraction angles and d-spacings is given in Table II below. The XRPD analysis was conducted on a PANanalytical X'Pert Pro Diffractometer on Si zero-background wafers. The acquisition conditions included: Cu $K_\alpha$ radiation, generator tension: 45 kV, generator current: 40 mA, step size: 0.02° 2θ.

TABLE II

| Diff. Angle [°2θ] | d-spacing [Å] |
|---|---|
| 4.279 | 20.6326 |
| 7.724 | 11.4362 |
| 9.212 | 9.5925 |
| 10.867 | 8.1348 |
| 12.824 | 6.8978 |
| 14.245 | 6.2124 |
| 15.576 | 5.6846 |
| 16.564 | 5.3476 |
| 16.878 | 5.2488 |
| 18.066 | 4.9062 |
| 18.601 | 4.7662 |
| 21.479 | 4.1337 |
| 22.076 | 4.0233 |
| 23.362 | 3.8046 |
| 23.999 | 3.705 |
| 24.249 | 3.6674 |
| 25.143 | 3.539 |
| 25.903 | 3.4369 |
| 27.092 | 3.2886 |
| 28.794 | 3.0981 |
| 30.704 | 2.9096 |

The differential scanning calorimetry (DSC) thermogram of the title compound was recorded on a TA Instruments Q100 Differential Scanning Calorimeter equipped with an autosampler and a refrigerated cooling system under 40 mL/min $N_2$ purge and is shown in FIG. 4. The experiments were conducted using a heating rate of 15° C./min in a crimped aluminum pan. The DSC thermogram of Compound C—Form 1 exhibits an endotherm with an onset temperature at about 141.7° C. A person skilled in the art would recognize that the onset temperature of the endotherm may vary depending on the experimental conditions.

The thermogravimetric analysis (TGA) thermogram of the title compound was recorded on a TA Instruments Q5000 Thermogravimetric Analyzer and is shown in FIG. 6. The experiments were conducted with 60 mL/min $N_2$ flow and a heating rate of 15° C./min. The TGA thermogram of Compound C—Form 1 exhibits approximately 1.25% loss of water below 75° C.

Compound C demonstrated the following properties:

No physical changes detected by XRPD analysis after 2 weeks at 25° C./60% RH in an open vessel, 40° C./75% RH in an open vessel, and 50° C./Ambient conditions in a closed vessel. Approximately 1.6% degradation by photolysis at 1×ICH solid state with no form change observed by XRPD. Solubility in Bio-Relevant Media and Britton-Robinson Buffer (BRB) Solutions

| Media | 24 h pH | 24 h solubility (mg/mL)[4] |
|---|---|---|
| Water | 6.7 | >1.8 |
| SGF[1] pH 1.6 | 1.8 | >1.7 |
| FaSSIF[2] pH 6.5 | 6.5 | >1.8 |
| FeSSIF[3] pH 6.5 | 6.5 | >1.7 |
| BRB pH 4 | 4.3 | >1.6 |
| BRB pH 7 | 7 | >1.9 |
| BRB pH 10 | 9.6 | >1.4 |

[1]Simulated Gastric Fluid
[2]Fasted State Simulated Intestinal Fluid
[3]Fed State Simulated Intestinal Fluid
[4]Unsaturated

What is claimed is:

1. A crystalline form of the benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide, wherein the crystalline form is characterized by an X-ray powder diffraction (XRPD) pattern comprising at least three diffraction angles, when measured using Cu $K_\alpha$ radiation, selected from a group consisting of about 4.3, 7.7, 9.2, 10.9, 12.8, 14.2, 15.6, 16.6, 16.9, 18.1, 18.6, 21.5, 22.1, 23.4, 24.0, 24.2, 25.1, 25.9, 27.1, 28.8, and 30.7 degrees 2θ.

2. The crystalline form of claim 1, wherein the crystalline form is characterized by an X-ray powder diffraction (XRPD) pattern comprising at least three diffraction angles, when measured using Cu K$_\alpha$ radiation, selected from a group consisting of about 4.3, 7.7, 9.2, 10.9, 12.8, 14.2, 15.6, 16.6, 16.9, 18.1, 18.6, 22.1, 24.0, 24.2, 25.9, 27.1, and 28.8 degrees 2θ.

3. The crystalline form of claim 1, wherein the crystalline form is characterized by an X-ray powder diffraction (XRPD) pattern comprising at least three diffraction angles, when measured using Cu K$_\alpha$ radiation, selected from a group consisting of about 4.3, 7.7, 15.6, 16.6, 16.9, 18.1, 18.6, 22.1, 24.0, 27.1, and 28.8 degrees 2θ.

4. A crystalline form of the benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide, wherein the crystalline form is characterized by an X-ray powder diffraction (XRPD) pattern comprising diffraction angles, when measured using Cu K$_\alpha$ radiation, of about 4.3, 7.7, 18.1, 18.6, 22.1, and 24.0 degrees 2θ.

5. A crystalline form of the benzoate salt of (S)-6-((1-acetylpiperidin-4-yl)amino)-N-(3-(3,4-dihydroisoquinolin-2(1H)-yl)-2-hydroxypropyl)pyrimidine-4-carboxamide, wherein the crystalline form is characterized by an X-ray powder diffraction (XRPD) pattern substantially in accordance with FIG. 2.

6. A pharmaceutical composition comprising the crystalline form according to claim 1 and a pharmaceutically acceptable carrier.

7. A pharmaceutical composition comprising the crystalline form according to claim 4 and a pharmaceutically acceptable carrier.

8. The composition of claim 6 wherein the composition is adapted for oral administration.

9. The composition of claim 8 wherein the composition is in the form of a tablet or capsule.

10. The composition of claim 7 wherein the composition is adapted for oral administration.

11. The composition of claim 10 wherein the composition is in the form of a tablet or capsule.

12. A method of treating mantle cell lymphoma in a human in need thereof comprising administering to said human an effective amount of the crystalline form according to claim 1.

13. A method of treating mantle cell lymphoma in a human in need thereof comprising administering to said human an effective amount of the crystalline form according to claim 4.

14. A method of treating mantle cell lymphoma in a human in need thereof comprising administering to said human an effective amount of the composition of claim 6.

15. A method of treating mantle cell lymphoma in a human in need thereof comprising administering to said human an effective amount of the composition of claim 7.

* * * * *